(12) United States Patent
Vazquez

(10) Patent No.: US 8,371,751 B2
(45) Date of Patent: Feb. 12, 2013

(54) LASER GUIDED PATIENT POSITIONING SYSTEM FOR CHIROPRACTIC X-RAYS AND METHOD OF USE

(76) Inventor: David Vazquez, San Luis Obispo, CA (US)

( * ) Notice: Subject to any disclaimer, the term of this patent is extended or adjusted under 35 U.S.C. 154(b) by 259 days.

(21) Appl. No.: 12/826,414

(22) Filed: Jun. 29, 2010

(65) Prior Publication Data

US 2011/0317808 A1    Dec. 29, 2011

(51) Int. Cl.
*A61B 6/08* (2006.01)
(52) U.S. Cl. ........................................................ 378/206
(58) Field of Classification Search .................. 378/205, 378/206
See application file for complete search history.

(56) References Cited

U.S. PATENT DOCUMENTS

| | | | |
|---|---|---|---|
| 4,426,726 A | 1/1984 | Cheetham | |
| 4,760,589 A | 7/1988 | Siczek | |
| 5,188,110 A * | 2/1993 | Sugimoto | 600/425 |
| 5,708,696 A | 1/1998 | Kantor | |
| 7,147,371 B2 | 12/2006 | Hecker | |
| 7,426,256 B2 | 9/2008 | Rasche et al. | |
| 7,613,494 B2 | 11/2009 | Hadley et al. | |
| 7,632,015 B2 * | 12/2009 | Stayman et al. | 378/206 |

* cited by examiner

*Primary Examiner* — Jurie Yun
(74) *Attorney, Agent, or Firm* — Trojan Law Offices

(57) ABSTRACT

A radiographic apparatus having a laser positioning system comprising three independent laser units for positioning a patient in three-dimension for the purpose of taking x-rays. Each laser unit is orthogonally oriented in respect to the others, such that the first laser unit projects a laser beam aligned with the x-ray beam in said first lateral direction, and the second laser unit projects a laser beam in a second lateral direction that is orthogonal to the first lateral direction, and the third laser unit projects a laser beam in a vertical direction that is orthogonal to both the first and second lateral directions. With the patient properly oriented by the laser system, x-ray films are taken that can be sequenced for radiographic animation analysis.

10 Claims, 11 Drawing Sheets

LASER GUIDED PATIENT POSITIONING SYSTEM FOR CHIROPRACTIC X-RAYS AND METHOD OF USE

FIELD OF THE INVENTION

The present invention is directed to a system and method of taking radiographic images, commonly known as x-rays. More particularly, the invention is directed to a system and method of using lasers in three dimensions to position patients for x-rays that can be sequenced for radiographic animation analysis.

BACKGROUND OF THE INVENTION

1. Conventional X-Ray Apparatuses and Methods

It is well known that the use of x-rays is vital in the treatment and diagnosis of patients, especially in chiropractic care. The effectiveness of radiographic diagnosis is critically dependent on the accuracy and quality of the x-ray images, which depend on the proper positioning the subject patient. The more precise the patient is aligned with the x-ray, the better is the resulting image. As such, the effectiveness of radiographic diagnosis is often compromised because it can be difficult to get the patient in just the right position and to orient the x-ray machine accordingly to take clear x-ray images.

Generally, an x-ray apparatus is comprised of an x-ray generator (commonly known as an x-ray tube) and a receptor (typically comprising a film cassette inserted in a grid cabinet, though recent technology has allowed for the images to be digitally captured).

The x-ray tube generates a beam that is projected onto the subject patient, who is interposed between the generator and the receptor. A collimator, which is a device that narrows the beam for improving the resolution of the x-ray image, is commonly used to collimate the beam to the proper size field of the patient's area of diagnostic interest. To further reduce the scatter associated with x-rays and produce a clearer image, a grid is used to block random rays and allow only rays generally in direct line to reach the film. Most importantly, it is imperative that the patient is properly positioned in alignment with the generator and the receptor to enable clear and accurate images of the patient's bones (or other diagnostic areas) to captured on the film.

2. The Use of X-Rays in Chiropractic Care

In chiropractic, subluxation is a physical misalignment that distorts the body, causing the spine to deviate from its normal position, which can result in pain and ailment throughout the whole body. To restore balance, evaluation and adjustment to the upper cervical is often necessary. As opposed to adjustments of the entire spinal column, specific adjustments can be made to the first cervical vertebra to bring it back to its proper position. The first cervical vertebra (also known as the atlas or C-1) is the topmost bone in the spine, being the first of the seven vertebrae in the spine known as the cervical spine (C spine).

Upper cervical adjustment depends upon precise biomechanics. This requires 3D composite x-rays to measure specific spinal misalignment in order to determine how best to adjust and correct it. Precisely taken x-rays are thus a critical part of ensuring the spinal correction is accurate and successful. Proper X-ray positioning is therefore essential to patient care.

In this regard, several cervical views are generally necessary for analysis of the upper cervical, including: lateral, base posterior, vertex, and nasium. From these x-ray views, a precise analysis of the position of the atlas vertebra is used to determine a vector for its adjustment.

This section will describe the radiographic views and how patients are currently positioned for these views.

A lateral cervical view is a side view of the upper cervical spine, taken to determine the relationship of the C-1 vertebra to the mastoid and to measure the atlas-plane-line angle (or "S-Lline" for taking a nasium film as described below). To take an x-ray in a lateral view, the patient is positioned with his shoulder against the lower part of the grid cabinet (also known as the bucky). Prior to positioning the patient for this view, the positions of the patient's ears are recorded against a horizontal line chart to determine the patient's head tilt as a component of his subluxation. The patient's chin is tucked so that the external auditory meatus is parallel to the inferior orbit, with the infra-orbial meatal line being parallel to the floor. The patient is then rotated using the movable chair in which he sits so that the head is perpendicular to the x-ray source. If the patient has an excessive head-tilt as determined using the horizontal line chart, the bucky and tube must also be tilted at the same angle, so the head remains lateral on the film. A string is used to make sure the tube is at the proper angle. The string is passed at the bottom of each earlobe when it is at the proper angle. The bucky is adjusted to correspond to the number of degrees the tube is tilted to give a true lateral position for the head in the horizontal plane on the resulting film. The central ray is centered to the area between C-1 and C-2 and the bucky is centered to the central ray. The patient's ears are aligned using the glabella bar and head clamps are applied to secure the patient. As setup, an x-ray image of the lateral cervical is taken.

A base posterior film is used to visualize the upper cervical spine from the "bottom up" point of view, in which the foramen magnum (occiput), atlas, and axis are seen as consecutive superimposed rings. The patient is seated facing the x-ray tube. The grid cabinet is tilted downward to a specified angle and positioned so that its center is perpendicular to the patient's vertex (the very top of the head). The tube is tilted upward and positioned so that the central ray coincides with the center of the film. This film is used to visualize the orientation and shape of the occipital condyles, the size and shape of the foramen magnum, the rotational angles of atlas and axis, and perhaps the severity of any existing constriction of the neural canal resulting from misalignment of atlas and/or axis.

A vertex film is analogous to the base posterior film described above except that the x-ray beam traverses the skull in the opposite direction. The patient is positioned facing the grid cabinet which is tilted upward to a specified angle. The patient's chin is made to settle on a special chin-harness that is attached to the grid cabinet. With the bucky thus angled, the patient's chin is elevated so there is a 90° relationship between the angle of the mandible and the sternocleidomastoid muscle. The tube is moved to a caudal angle so that the central ray is perpendicular with the floor of the skull at the atlas traverse process. The central ray is directed at right angles through a line passing from the patient's superior orbit to the tip of the transverse process, the angle of which is verified by using a string. In other words, the x-ray tube is raised above the patient's head and angled downward so that the central ray traverses through the patient's vertex and coincides with the center of the film. The vertex view is taken to produce a clear view of the atlas, nasal septum and C-2 spinal canal to determine atlas rotation and C-2 spinal canal rotation.

The purpose of a nasium film is to obtain an optimal view of all the structures at the proper angle and exposure so as to enable accurate film analysis. To take a nasium film, the atlas has to be properly positioned on the film by measuring the S-line off lateral and finding the landmark for C-1 so that the central ray is at the proper angle. The goal of this positioning effort is to visualize atlas precisely "head-on" therefore the tube is tilted to an angle that is perpendicular to the atlas plane line angle measured on the lateral film. Accordingly, the proper S-line is determined from the lateral cervical film. Next, the correct orientation of the atlas transverse process (atlas TP) is determined so that the atlas can be properly positioned on the film. With the patient facing the tube, the bucky is tilted so that it is at the same approximate angle as the back of the head and shoulders. The patient's head is positioned approximately in the center of the bucky. The tube is angled so that the central ray will travel along the S-line and will exit the patient at the level of the atlas transverse process. The central ray must enter the film ½ inch above its center. A string is extended from the tube to the bucky where the central ray will hit the bucky so as to make sure that the patient's head is correctly oriented and that the central ray is consistent with the S-line. With the head secured by clamps, the nasium film is taken.

An APOM (anterior to posterior open mouth) film is used to visualize the upper cervical spine from the anterior to posterior point of view. The patient is positioned with the back of his head against the grid cabinet. The x-ray tube is positioned at a specific distance from the grid cabinet and the central ray of the x-ray beam is aimed so that it intersects the level of the C1 vertebra. The film is captured (with the patient open-mouthed) to get a clear shot of the upper cervical spine to assess atlas and axis laterality as well as to discern any anatomical abnormality or trauma.

Current radiographic methods for chiropractic diagnosis, particularly of the upper cervical spine, based on taking the x-ray views described above, suffer from inaccuracies due to the subjective positioning of the patient from view to view. This results in radiographic images that can be inaccurate or unclear. Because upper cervical adjustment depends upon precise biomechanics, a system and method are needed to objectively and precisely position patients in respect to the different radiographic views described above.

Further, current radiographic methods of the upper cervical spine are based on using x-rays to determine static misalignment of the vertebrae, rather than determining restrictions in the motion of the cervical vertebrae which can only be discerned by taking range-of-motion radiographs. That is, such traditional radiographic methods for determining chiropractic listings of the upper cervical spine characterize misalignments based on films in the neutral position. These methods do not consider active biomechanical dysfunction. Understanding that the most accessible component of the subluxation complex is articular fixation, a new method that characterizes fixation based on dysfunction would improve confidence in the listing attained and the quality of the care delivered.

SUMMARY OF THE INVENTION

Accordingly, it is a primary object of this invention to provide a system and method of taking x-rays for radiographic animation studies.

It is an object of this invention to provide a system and method for exact positioning of patients for radiography by using a system of lasers to reduce or eliminate the influence of positioning errors.

It is an object of this invention to provide a system and method for positioning patients for unidirectional range-of-motion radiography due to the system's ability for positioning at exact degree increments of motion in one plane while holding the other two planes constant so as to generate sets of x-ray films that can be sequenced using computer animation software for the purpose of assessing biomechanical dysfunction of the visualized osseous articulations upon said motion.

It is an object of this invention to provide a system and method for precisely targeting and centering a relatively narrow anatomical area of interest onto an x-ray film.

It is an object of this invention to provide a system and method to facilitate x-ray positioning by eliminating the subjective and cumbersome aspects associated with the use of current positioning aids.

The present invention is directed to solving certain technical problems commonly encountered in upper cervical chiropractic radiography. One problem involves the reproducibility of patient positioning Many practitioners believe that exact reproduction of a patient's position for different radiographic views is not possible. The reason that current methodologies are inaccurate is that they are not based on objective tools and protocols. The method of the present invention, however, is capable of accurately reproducing a patient's positioning because it is based on objective measurements taken with laser-guided precision in all three dimensions of space.

Another shortcoming that is overcome by the present invention is the positioning of patients for range-of-motion radiographic series. Currently, some chiropractors use range-of-motion series to assess the state of biomechanical function in a patient's upper cervical spine. These practitioners analyze such radiographic series with an understanding of the normal biomechanical coupled motion that occurs with these motions. The chiropractors may determine adherence to normal biomechanics based on changes in position of the atlas and axis from one film to the next in a series. In this way, they are able to assess the direction of restricted motion exhibited by atlas and/or axis and this ultimately leads to the listing they use to adjust the patient. The main problem with this method of analysis lies with proper positioning of the patient during film capture; that is, practitioners attempt to isolate the motion in question but have no way of ensuring that the motion is pure. For example, when the patient is asked to tilt his head to the left (for the left-lateral flexion film), the tendency of the patient is to also extend the head as well as to rotate it to the right. These additional motions, although slight, taint the emergent films and alter an accurate representation of the patient's biomechanics which decreases confidence in the assessment as well as the listing used to adjust the patient. In other words, the chiropractor cannot be completely certain that he is delivering the correct adjustment to the patient.

Accordingly, the present invention will allow for patient positioning in pure range-of-motion film series. The three independently movable laser units of the system account for all three dimensions of space. One unit can be moved to align the end range of a given motion in one dimension while the other two units are held static to ensure the patient does not change position with respect to the two other dimensions. The design of this system also allows the user to accurately measure the angle of this end range by way of calibrated markings on the respective laser units that coincide with the projected laser line. This system greatly increase the accuracy of biomechanics exhibited by the emergent film series and thus that of the radiographic analysis, both of which add to the certainty that the correct adjustment will be made to the patient.

Another shortcoming overcome by the present invention involves how films are viewed for analysis. Currently, the three films that comprise a series (e.g. left-lateral flexion, neutral, and right-lateral flexion) are visualized side by side on a view box or, if they are digital films, individually on a computer screen. The neutral film is viewed first to assess head-tilt and to determine if the displacement of atlas and axis are consistent with that head tilt according to normal biomechanical coupled motion. For example, if the patient exhibits a right head-tilt on the neutral film, then the expected lateral displacement of atlas would be to the right, that of axis (dens) would be to the left, and that of the spinous process of axis would be to the left as well. If any of these displacements are not exhibited, then it is inferred that motion is restricted in that direction. Next, the other two films are assessed in the same fashion; the difference is that in these cases, the head tilt is purposely induced and thus any restricted motion is exaggerated. However, as previously mentioned, the patient positioning for these films is not perfect and so any alteration in biomechanics observed may be due to positioning error.

In the present invention, animation software allows for the films to be sequenced with a consistent center of reference. Having a static center of reference will allow for the measurement (not just visualization) of the displacement exhibited by occiput, atlas, and axis that result from pure range-of-motion. Using these measurements, restricted motion will be characterized numerically which will increase the objectivity of the assessment.

Currently, a method exists to empirically assess spinal dysfunction, which is based on taking x-ray films of the upper cervical spine at its end ranges of lateral flexion as well as in the neutral position. This film series is subjectively analyzed for adherence to normal biomechanical coupled motion. These findings allow the chiropractor to adjust patients with the specific aim to restore normal motion.

A system and method according to the present invention will improve this method's objectivity by using a laser-assisted patient-positioning system to set up the films and a computer animation program to analyze them. The system will improve the accuracy of the films and the animation program will facilitate the subsequent analysis. Using the system described herein, patients can be strategically radiographed to generate a pool of films that represent various views and directions of motion. Several animation sequence variations can be generated from this pool. These animations can be analyzed to determine which view and direction of motion most clearly elucidates biomechanics. A calculation scheme is used to relate the unilateral angular displacement of a given motion to the resulting linear displacement of the upper cervical spine's anatomy. This calculated value represents an internally relevant objective parameter that describes a patient's dysfunction.

A precision alignment system for radiographic animation according to the present invention comprises a radiographic imaging apparatus (x-ray machine) that employs three independent laser units to aid in precisely positioning a subject patient for radiography. The three laser units are mounted in such a way that the laser line projections coincide with the alignment of the radiographic apparatus's frame an in all three dimensions (X, Y, and Z) with respect to the primary beam of the x-ray source. The laser system functions to aid in the precise positioning of the patient with respect to the primary beam of the x-ray source so as to minimize or eliminate magnification distortions on the resulting x-ray film which can result from coordinate and/or rotational positioning errors.

A. The X-Ray Apparatus

The x-ray apparatus of the present invention is comprised of the standard components of an x-ray machine, including an x-ray tube and a grid cabinet, both mounted to a frame. The x-ray tube is provided with a collimator. The collimator is a box-like device attached to the square aperture of the lead x-ray tube housing. The face of the collimator typically has a square opening protected by a clear plastic or glass window (collimator aperture) through which the x-ray beam exits after collimation has occurred.

B. The Laser System

The laser system comprises three laser-emitting units. This three-unit laser system allows for accurate and measurable positioning of patients for radiographic studies by accounting for all three dimensions of space. The system substantially increases the accuracy of the emergent radiographic films as well as their subsequent analysis. The system also allows for studying biomechanical changes that result from movement along one dimensional plane while holding the other two constant. The three laser units are referred to as: (1) the Collimator Laser Unit, (2) the Wall Laser Unit, and (3) the Overhead Laser Unit.

1) The Collimator Laser Unit

The Collimator Laser Unit is comprised of two laser emitters mounted on the x-ray tube collimator for projecting two independently movable laser lights towards the patient along the same vector as the x-ray beam. The emitters are independently mounted on a track mechanism that allows for the positioning of each emitter at an angle in respect to the central axis of the x-ray beam. For example, if the emitters are set in perpendicular positions (i.e. one at 0° and the other at 90°), then the emergent laser lines will appear as a crosshair upon the patient. As referenced herein, where the emitter is set at 0° it is referred to as the "vertical component" and where the emitter is set at 90° it is referred to as the "horizontal component". It should be understood that regardless of the angle at which the emitters are set, the projected lasers always intersect at the central ray of the x-ray beam.

2) The Wall Laser Unit

The Wall Laser Unit comprises a laser emitter as shown in FIG. 4. The emitter is equipped with a crosshair pattern generator, which is secured and calibrated in such a way that the center of the projected crosshair coincides precisely with the center of a circular plate on the surface on the emitter as shown in FIG. 5. The circular plate is rotatable about its center axis by turning the cylindrical housing of the generator. Since the center of the projected laser crosshair coincides with the rotational center of the circular plate, the crosshair projection can also rotate on its center as the generator is turned. The ring articulation on the circular plate is scored with graduated markings representing one-degree increments. In juxtaposition with the degree markings on the ring, the circular plate is also scored with four radial linear markings that correspond to the four cardinal lines of the projected laser crosshair. This allows for the rotational positioning of the projected laser crosshair to any degree from the centerline (0°). Further, the emitter is mounted on a frame having a track system that allows it to translate vertically and/or horizontally. Each track is equipped with a locking mechanism that locks the laser unit in place once the desired location is reached. As such, the laser unit is capable of vertical, horizontal, and rotational movements.

The Wall Laser Unit is mounted on a wall (or other structure) adjacent to the grid cabinet for projecting a laser crosshair in a lateral direction towards the patient. In other words, the laser beam is directed towards the patient from the side in a direction that is orthogonal to the direction of the central x-ray beam. For example, if the patient is facing the x-ray tube, the laser line will project across the side of the patient's face.

3) The Overhead Laser Unit

As shown in FIG. 6, the Overhead Laser Unit, which includes an emitter identical to that of the Wall Laser Unit, is mounted above the subject patient by way of a horizontally level longitudinal track. The track is centered so that it overlies the midline of the grid cabinet. The midline of the grid cabinet is aligned to precisely coincide in the vertical plane with the central x-ray beam. The Overhead Laser Unit thus runs in line with the central x-ray beam. As mounted, the Overhead Laser Unit hangs above the patient and projects a laser crosshair downward across the top of the patient's head and shoulders.

The laser unit has on one surface a mechanism for articulating with the undersurface of the track, which allows it to traverse or glide across the full length of the track. This mechanism also allows for locking of the laser unit in place once the desired position is reached. Along its track-articulating mechanism, the laser unit has a mark that is juxtaposed with the graduated distance markings along the track and also coincides with the center point of the laser crosshair. This allows the operator to measure the location of crosshair center point as a distance from the center of the grid cabinet.

The laser system is installed and calibrated onto the x-ray apparatus set up for upper cervical chiropractic technique radiographs as described above. Using the laser system to precisely position and orient the patient, films are taken to produce range-of-motion radiographs based on the lateral, vertex, and nasium views. The digital films are imported into a computer and converted into the frames of an animation sequence. The animation sequence is analyzed to determine biomedical dysfunction.

DETAILED DESCRIPTION OF THE INVENTION

Figure 1:
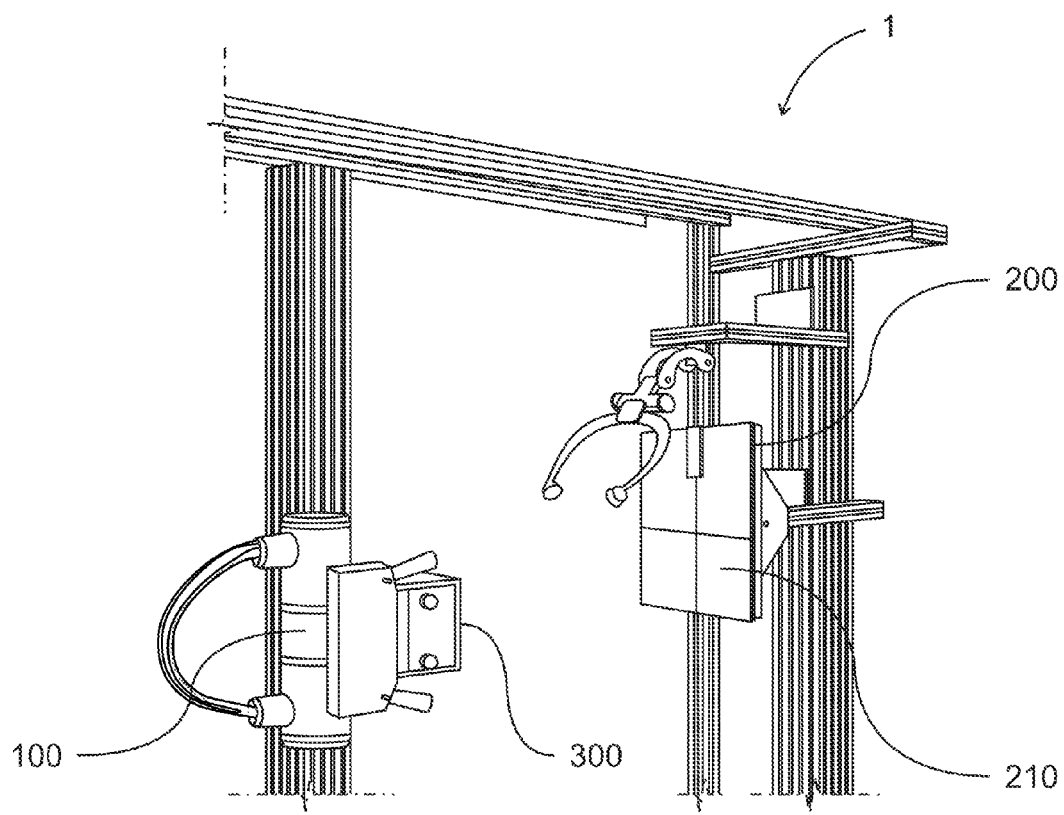
FIG. 1 is a perspective view of an x-ray apparatus according to an embodiment of the present invention.
Figure 2:
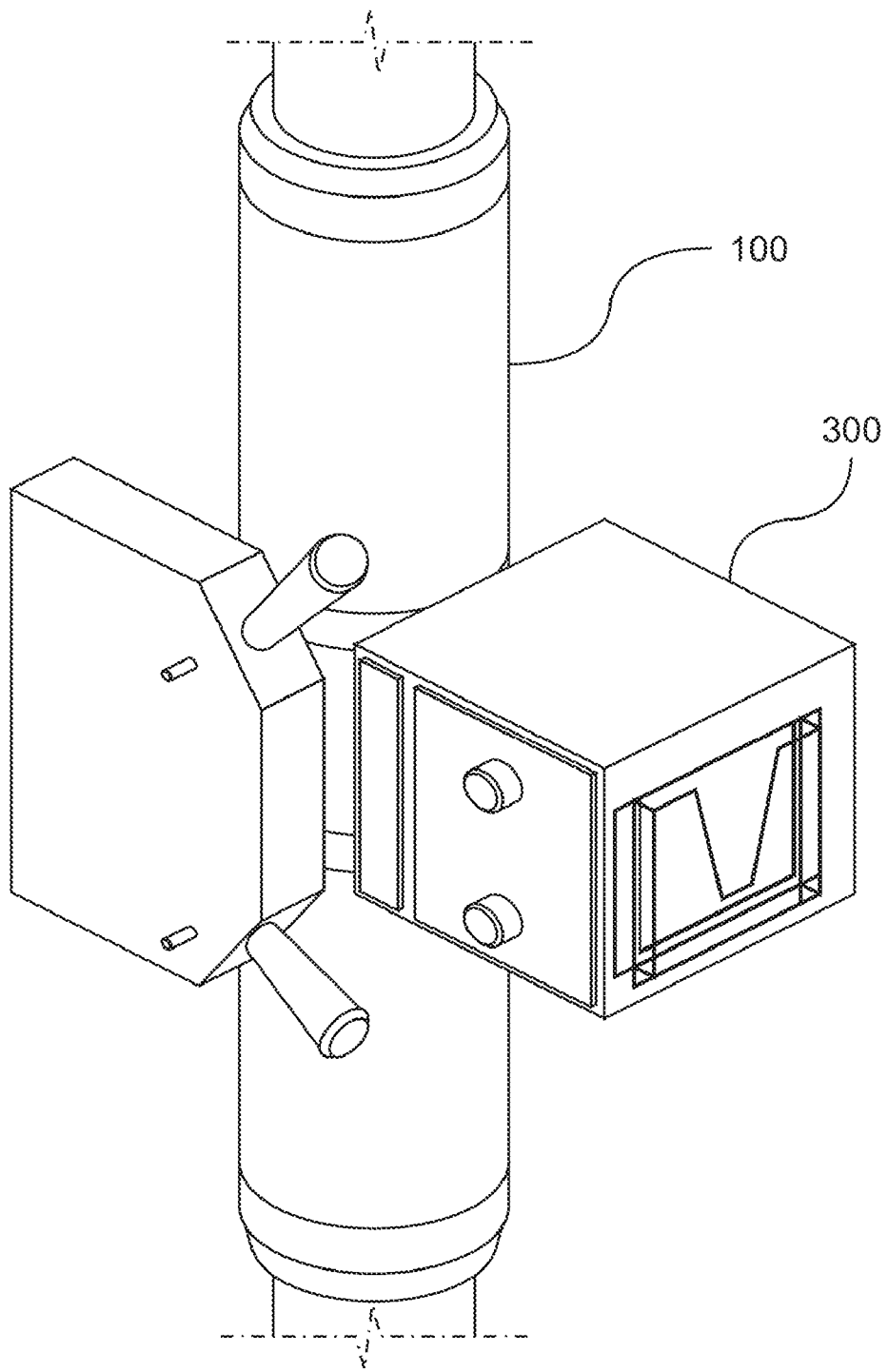
FIG. 2 is a perspective view of a portion of the x-ray apparatus showing a collimator.

As shown in the drawings, a laser system according to an embodiment of the present invention is associated with a radiographic apparatus typically used for taking upper cervical x-rays. However, it will be understood that the system and method described herein can be used with any medical, industrial, and other type of x-ray machines where precise alignment of the subject is required.

In a preferred embodiment of the invention as shown in FIG. 1, a radiographic apparatus 1 includes an x-ray tube 100 and a grid cabinet 200. The x-ray tube 100, fitted with collimator 300, is aimed in a first lateral direction for projecting an x-ray beam at the grid cabinet 200.

Figure 3A:
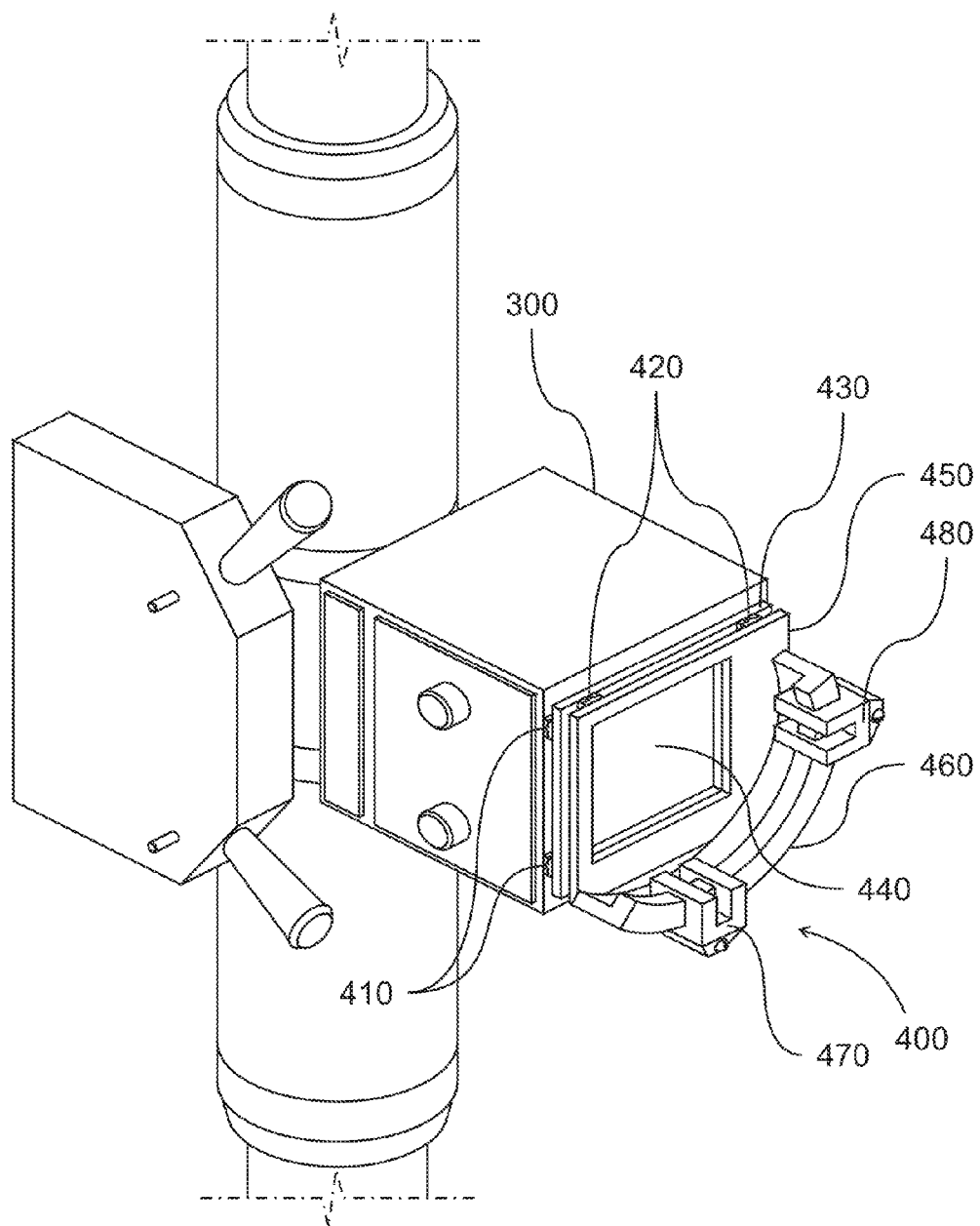
FIG. 3A is a perspective view of the Collimator Laser Unit.
Figure 3B:
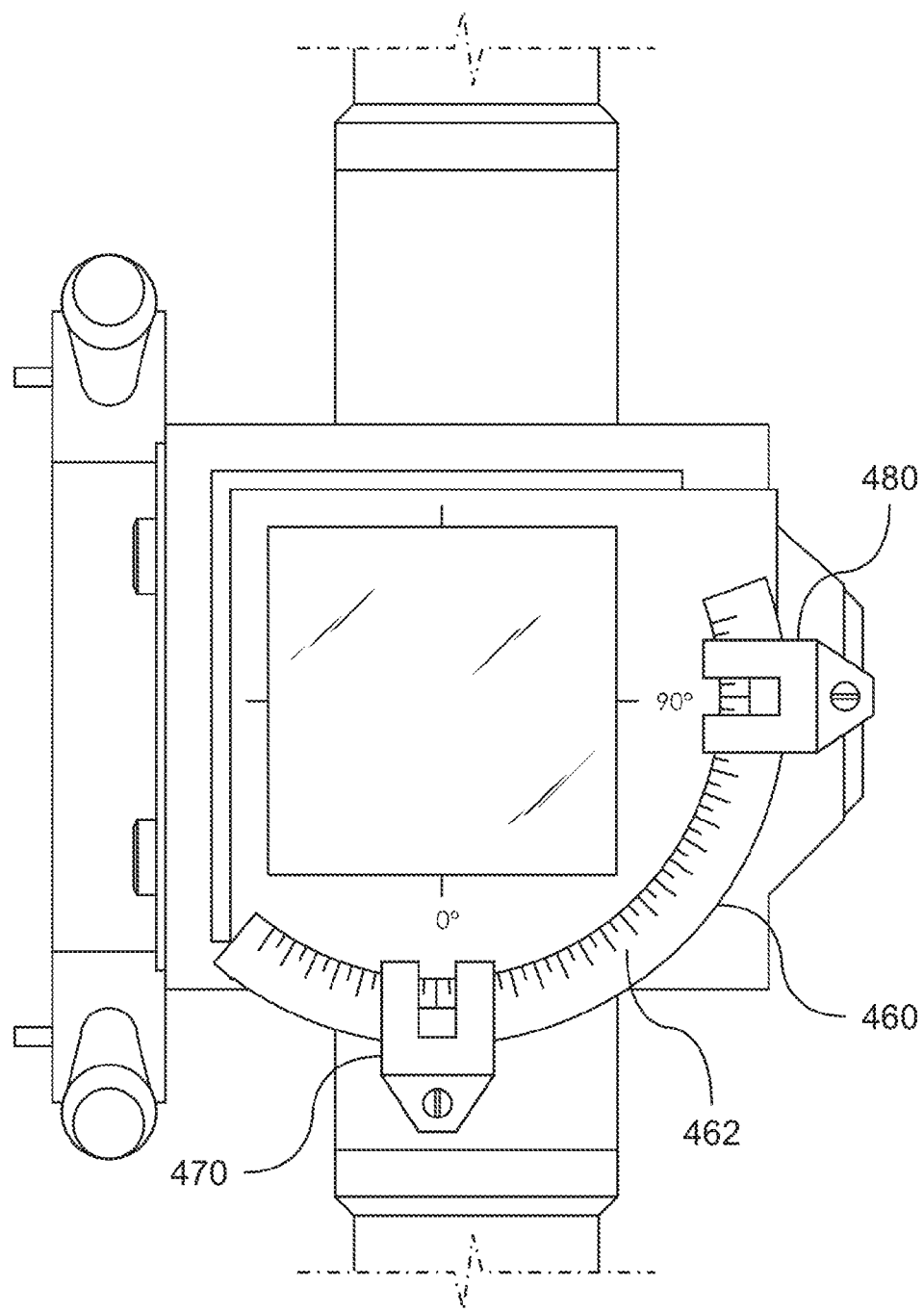
FIG. 3B is a front view of the Collimator Laser Unit attached to the collimator.

A Collimator Laser Unit 400 is mounted on the face of the collimator 300 as shown in FIGS. 3A and 3B. It is mounted on collimator 300 by an attachment mechanism comprising a system of horizontal and vertical tracks 410, 420 that allows it to be centered with respect to the x-ray beam. Two horizontal tracks 410 attach above and below the top and bottom margins (respectively) of the collimator aperture 300. A first plate 430 articulates with tracks 410. Two vertical tracks 420 attach to the outside surface of first plate 430 on opposite sides of its square opening 440. A second plate 450 articulates with vertical tracks 420. This allows for vertical translation of second plate 450. Attached to the outside surface of second plate 450 is a circular track 460 having a radial center that coincides with the center of the square opening 440.

The Collimator Laser Unit 400 has two laser emitters 470, 480 each equipped with a single-line pattern generator. The emitters 470, 480 are independently attached to the circular (or semi-circular) track 460, such that each emitter 470, 480 can independently translate along the circumferential path of track 460. As described above, track 460 is centered with respect to x-ray tube 100 such that its radial center is coaxially aligned with the central x-ray beam.

The laser lines from emitters 470, 480 are projected along a vector that is parallel to and points in the same direction as the central x-ray beam. Each emitter 470, 480 is aligned with a radial line as shown in FIG. 3B. As such, translating the emitter 470 or 480 along circular track 460 would result in a pivoting motion by the projected laser line centered precisely on the virtual point target of the x-ray beam. The face of track 460 is scored with graduations 462 representing one-degree increments of axial rotation centered at the x-ray beam. As shown in FIG. 3B, the gradation in line with the vertical plane is designated as "0" degrees and the gradation in line with the horizontal plane is designated as "90" degrees. Setting the two laser emitters 470, 480 at 90° to each other would result in their line projections intersecting in a crosshair pattern that is coaxial with the x-ray beam.

Figure 4:
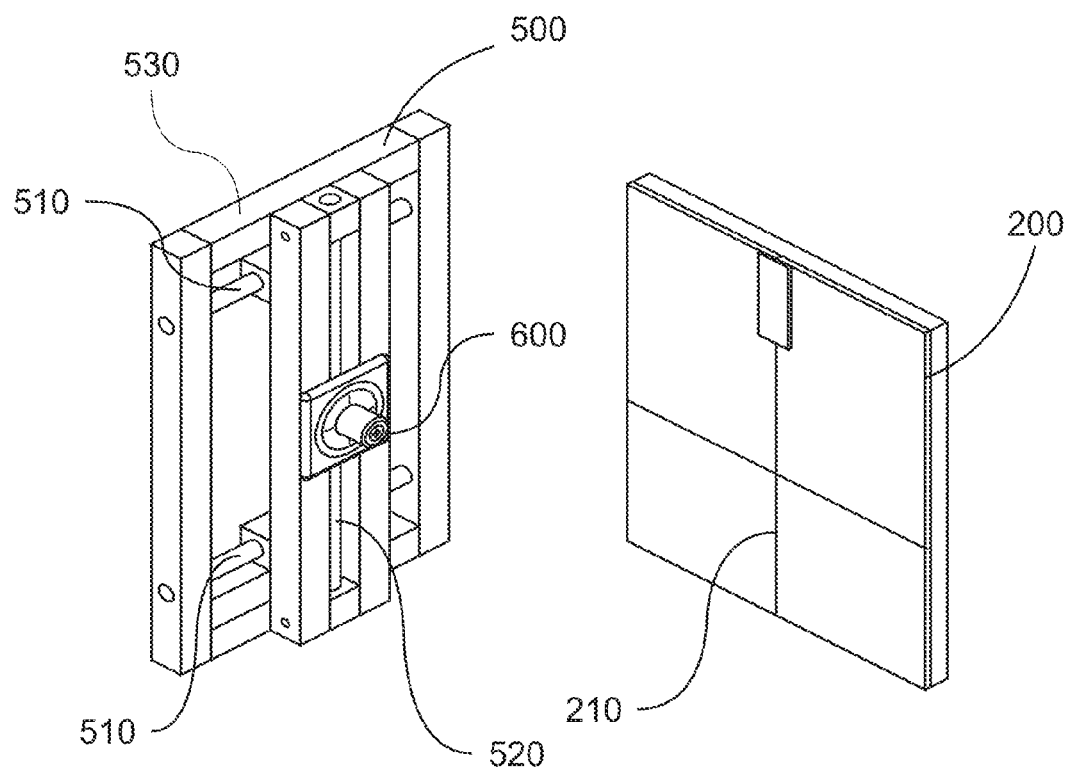
FIG. 4 is a perspective view of the Wall Laser Unit.
Figure 5:
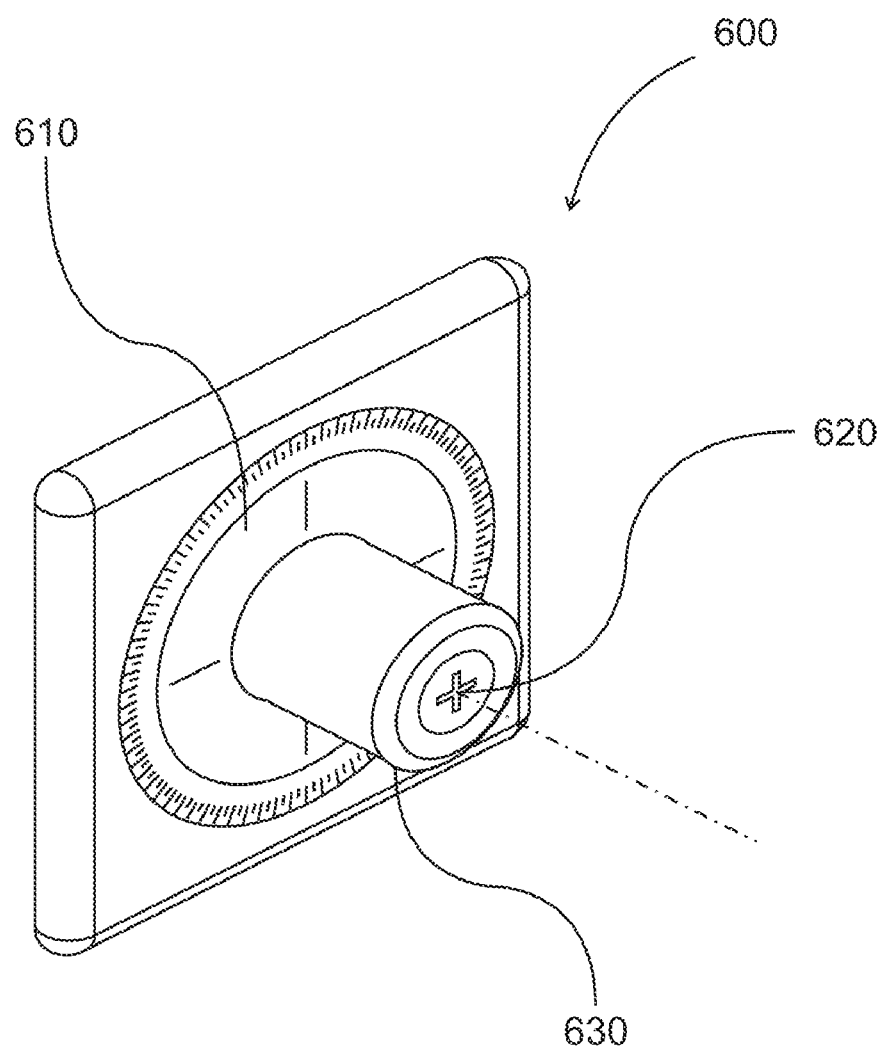
FIG. 5 is a perspective view of a laser emitter.

As shown in FIG. 4, a Wall Laser Unit 500 comprises a laser emitter 600 having a crosshair line pattern generator. The emitter 600 is centrally mounted a circular plate 610 in such a way that the center of the projected laser crosshair 620 is coaxial with the center of the circular plate 610. The circular surface is rotatable by turning the cylindrical housing 630 of the emitter 600. This allows for the rotational positioning of the of the projected laser crosshair to any degree from the centerline (0°).

The Wall Laser Unit 500 is mounted on a wall (or other structure) adjacent to grid cabinet 200. The emitter 600 is mounted on a set of vertical and horizontal tracks 510, 520 that permit it to translate vertically and horizontally within attachment frame 530. The Wall Laser Unit 500 projects a laser crosshair in a lateral direction towards the patient that is orthogonal to the x-ray beam.

Figure 6:
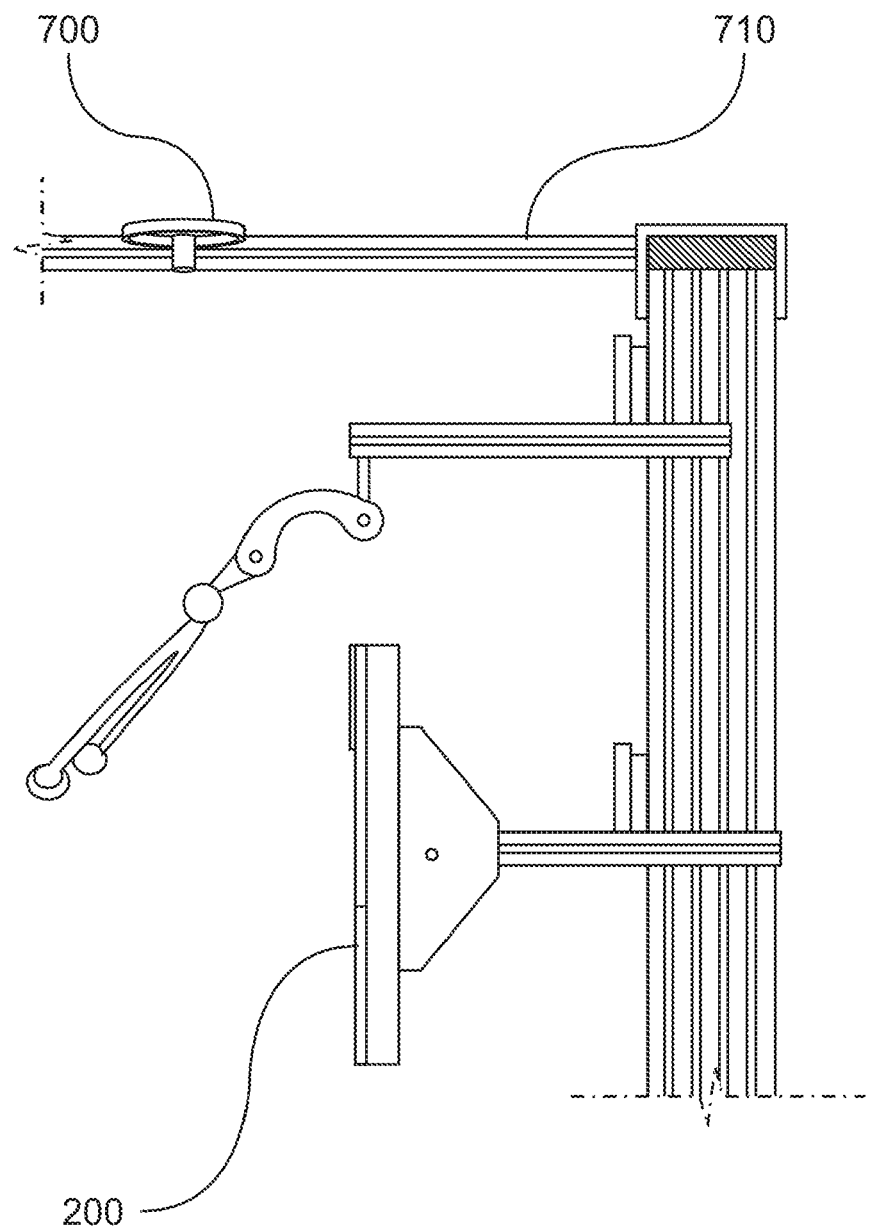
FIG. 6 is a side view of an x-ray apparatus showing the Overhead Laser Unit.

As shown in FIG. 6, the Overhead Laser Unit 700 is moveably mounted on horizontally level longitudinal track 710. The track 710 is centered so that it overlies the midline 210 of grid cabinet 200. The Overhead Laser Unit 700 is mounted above the patient, such that it projects a laser crosshair downward across the top of the patient's head and shoulders.

The Overhead Laser Unit 700 employs the same emitter 600 as employed by the Wall Laser Unit 500. The emitter 600 has a mechanism (not shown) for articulating with the undersurface of track 710, which allows it to traverse or glide across the full length of track 710. This mechanism also allows the laser unit 600 to be locked in place once it reaches the desired position. The emitter 600 has a mark, coinciding with the center point of the laser crosshair 620, which is juxtaposed with the graduated distance markings along the track to allow measurement of the location of the crosshair center point as a distance from the center of the grid cabinet 200.

The laser system is installed onto and calibrated with the x-ray apparatus as described. Using the laser system to precisely position and orient the patient, films are taken to produce range-of-motion radiographs based on various radiographics views, including the lateral, vertex, and nasium views described above. However, in contrast to the conventional methods of taking the various radiographic views described above and how patients are positioned for these views, the following describes the procedures for taking radiographic views according to the invention herein.

1) Lateral Cervical View

Figure 7A:
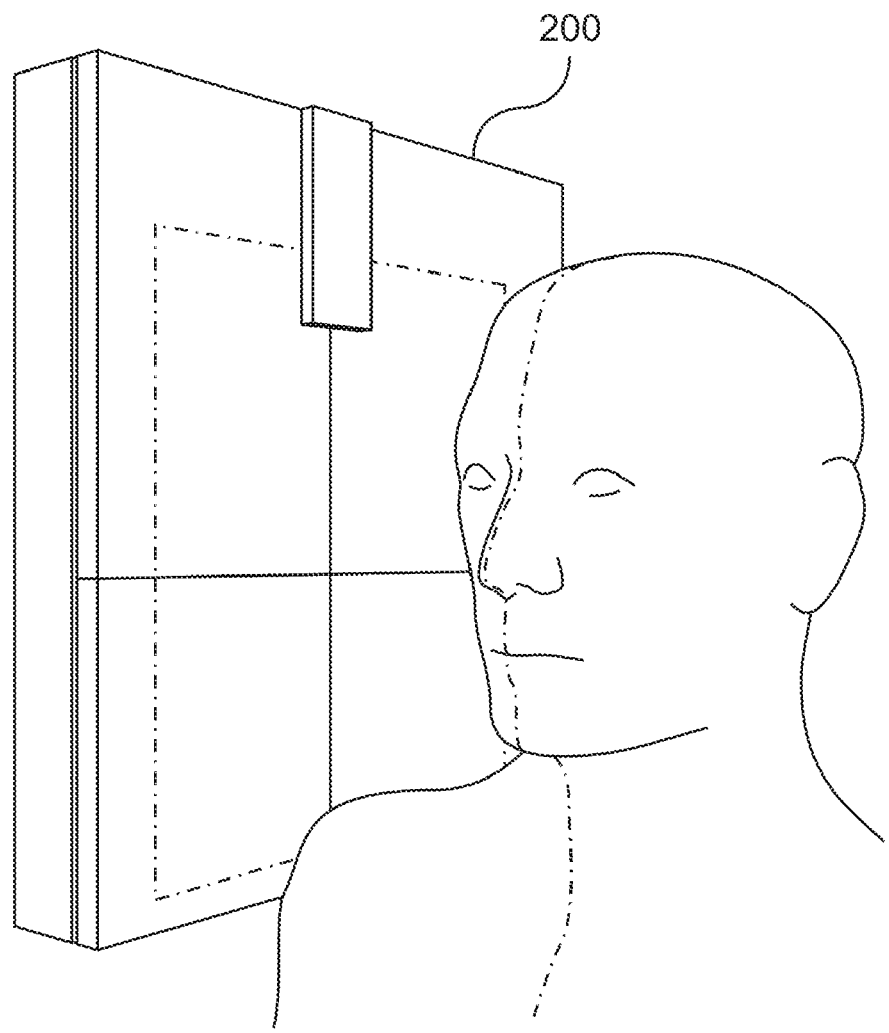
FIG. 7A is a view of a subject positioned facing the Wall Laser Unit for an x-ray in the lateral view.
Figure 7B:
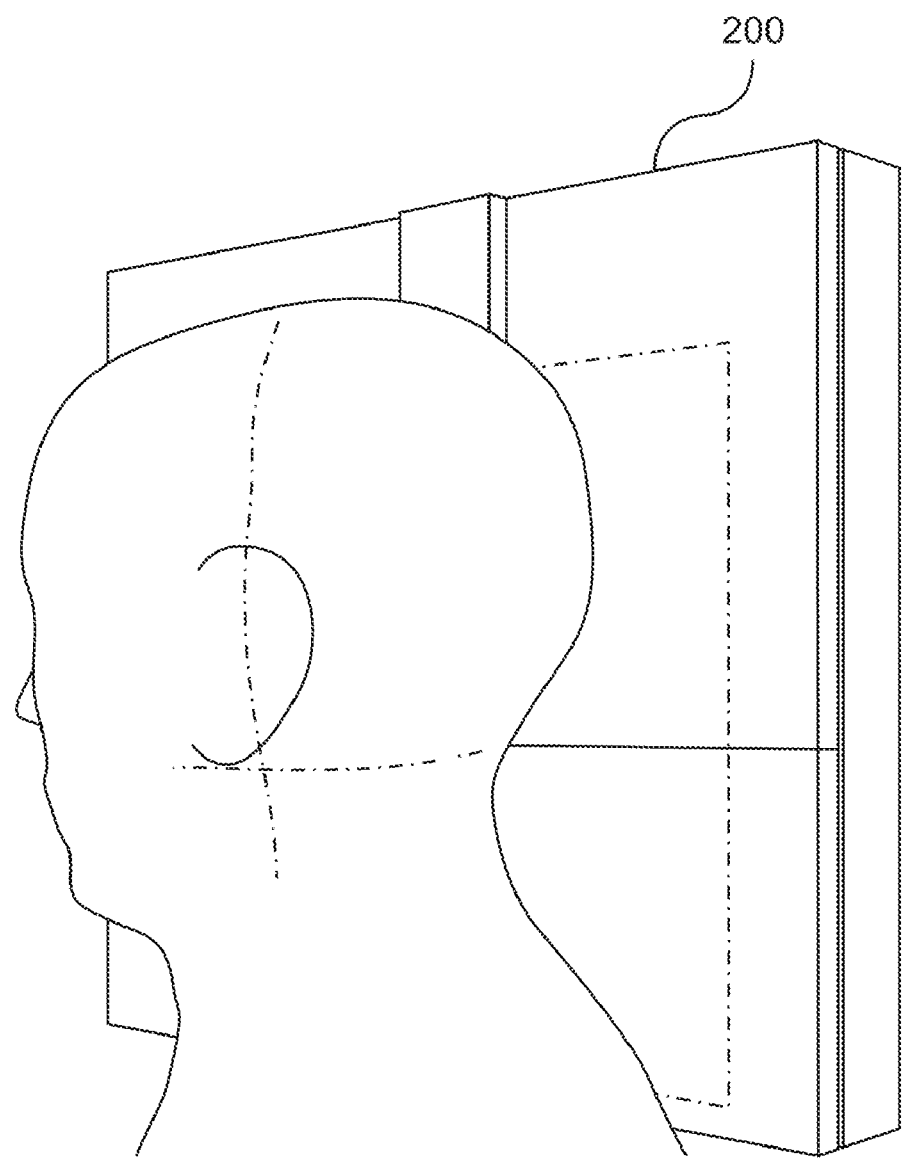
FIG. 7B is a view of a subject positioned facing the Wall Laser Unit for an x-ray in the lateral view.
Figure 8A:
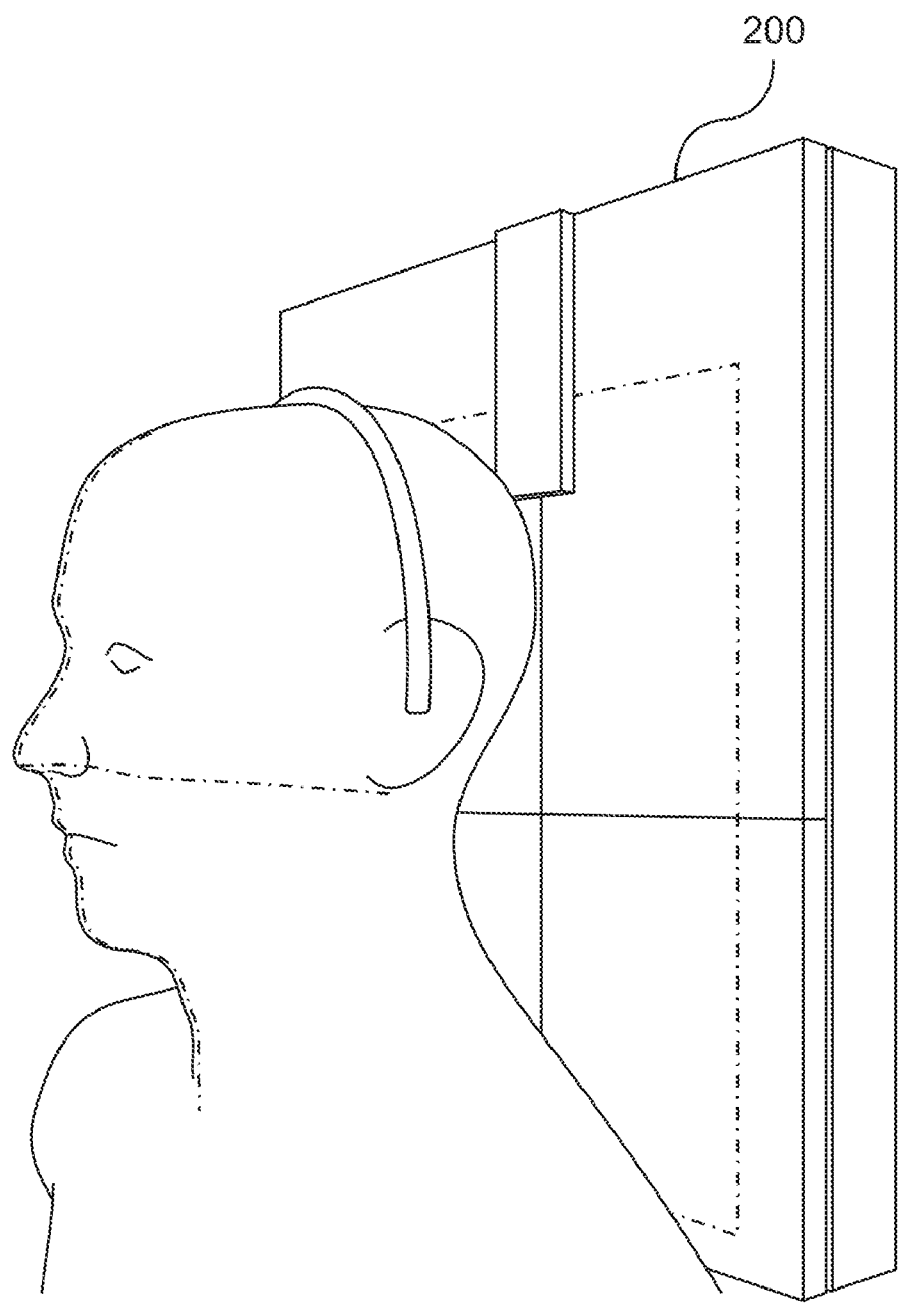
FIG. 8A is a view of a subject positioned facing the Collimator Laser Unit for an x-ray in the nasium view.

To prepare the subject patient for a lateral cervical film, the patient is marked on the antero-lateral aspect of both cheeks that is in line with the inferior orbital margin. Extrapolating a horizontal line from that point laterally to the transition zone where anterior meets lateral, a small horizontal dash is marked to represent this line at the transition zone. A buck shot is secured to each external auditory meatus with clear tape. As shown in FIGS. 7A and 7B, the patient is positioned facing the Wall Laser Unit 500 with his right shoulder touching the grid cabinet 200. The patient is to wear a headband across the top of the head (bisecting the head in the coronal plane, as shown in FIG. 8A) so that the tips are in line with the mastoid processes (and C1 TP). The patient is translated so that the vertical laser component of the Collimator Laser Unit 400 is in line with the lateral aspect of the headband (which is in line with C1 TP). The x-ray tube 100 (set at 0° tilt) is translated vertically until the horizontal laser component of the Collimator Laser Unit 400 is at the level of the buck shot. The patient's chin is lowered until the infraorbital marking intersects the laser line. Thus, the laser line, which is set to 0° horizontal, connects the buck shot to the infraorbital marking. The headband is adjusted so that it is in line with the vertical laser component of the Collimator Laser Unit 400. With the Overhead Laser Unit 700 set to 0° coronal (relative to the patient), the patient is rotated until the laser line precisely matches the headband. The laser line on the Wall Laser Unit is set to 0° vertical, and the patient is positioned such that the laser line bisects the patient's face as shown in FIG. 7A. This ensures the absence of head tilt and/or rotation. The x-ray tube is positioned so that the laser crosshairs intersect the C1 TP. The bucky 200 is positioned so that the central ray is at the center of the film using the horizontal Collimator Laser Unit 400 laser line. The film is then taken.

2) Vertex View

For a vertex film, the patient is positioned facing the grid cabinet 200. The vertical laser component of the Collimator Laser Unit 400 is used to center the patient. The bucky 200 is translated vertically so that the patient's chin is made to rest on a special chin-harness that is attached to the bucky 200. The bucky 200 angled to establish a 90° relationship between the angle of the mandible and the sternocleidomastoid muscle. The Wall Laser Unit 500 is positioned so that its laser line traverses the both buck shot and the superorbital ridge. This angle is noted by reading the markings on the Wall Laser Unit 500. The x-ray tube 100 is set to an angle that is perpendicular to the angle noted above. The Overhead Laser Unit 700 is set to 0° sagital (relative to the patient). The Overhead Laser Unit 700 is translated so that the laser line projects down the center of the patient's face and bisects the head. The x-ray tube 100 is positioned so that the crosshair of the Collimator Laser Unit 400 traverses the C1 TP and projects one inch below the center of the film (i.e. the vertex line). The central ray is thus directed at right angles through a line passing from the patient's superior orbit to the tip of the transverse process, the angle of which is verified by using a string. The vertex view is taken to produce a clear view of the atlas, nasal septum and C-2 spinal canal to determine atlas rotation and C-2 spinal canal rotation.

3) Nasium View

Figure 8B:
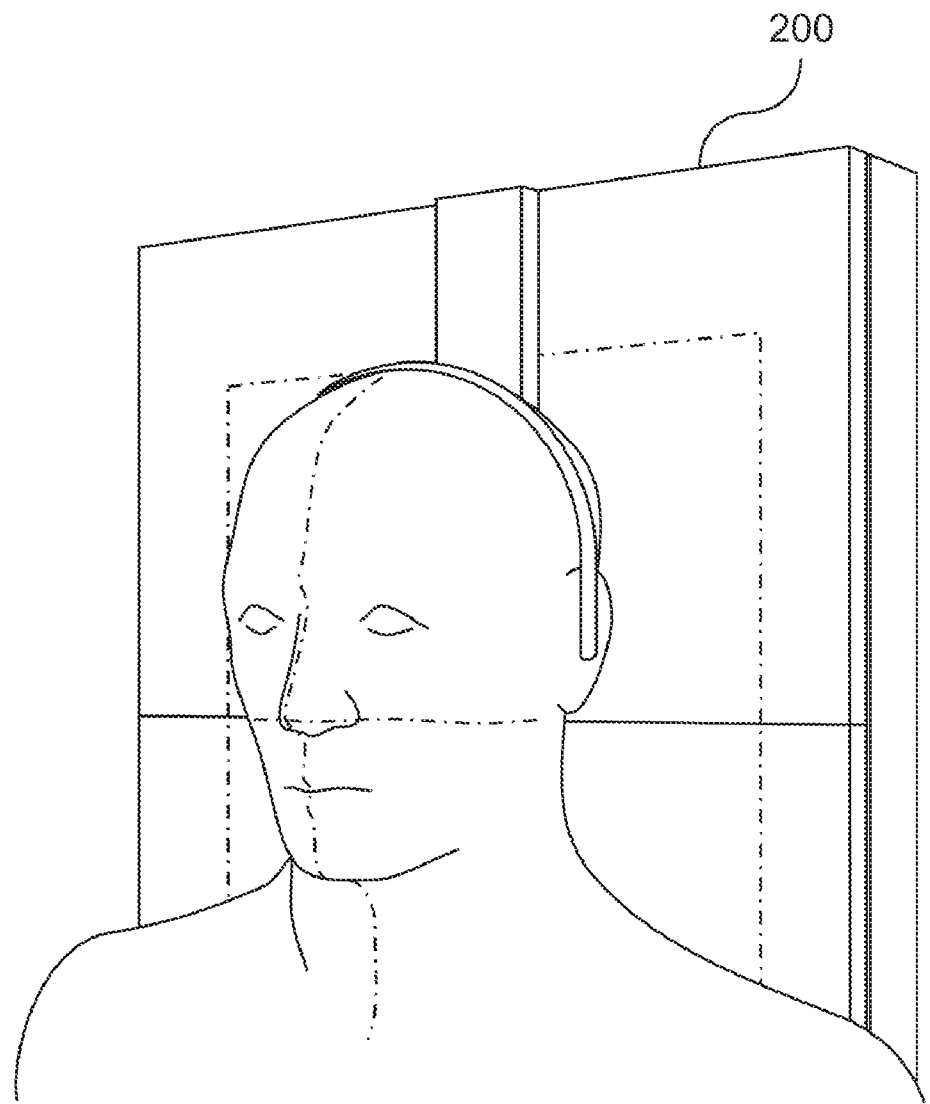
FIG. 8B is a view of a subject positioned ng the Collimator Laser Unit for an x-ray in the nasium view.

The atlas plane angle is measured and noted from the lateral film. The x-ray tube 100 is tilted to this angle. The patient's head is set in the neutral position. The Wall Laser Unit 500 is set to 0° horizontal and the laser line is aligned to the buck shot. The patient's chin is moved downwardly (without disturbing the head tilt) until the laser line intersects the infraorbital marking. The patient is translated to be approximate to the bucky 200. The bucky 200 is vertically and angularly positioned so that it matches the contour of the patient's head and shoulders. The Overhead Laser Unit 700 is rotated to 0° coronal (relative to the patient) and translated so that it intersects the center of the headband worn by the patient. The patient's rotational position is adjusted so that the headband matches the laser light. Without changing the tube tilt set earlier, the tube 100 is positioned so that the horizontal laser line of the Collimator Laser Unit 400 traverses the C1 TP as shown in FIG. 8A. The patient is translated laterally so that he is centered to the vertical laser line of the Collimator Laser Unit 400 as shown in FIG. 8B. The bucky 200 is adjusted vertically so that the horizontal laser line of the Collimator Laser Unit 400 matches the center of the film. The film is taken.

Using the laser system to precisely position the patient in all three dimensions greatly improves the accuracy of the lateral, vertex, and nasium views, so as to enable a more precise analysis of the biomechanics necessary for adjustment of the atlas vertebra.

Further, the digital films can be imported into a computer and converted into an animation sequence to produce range-of-motion radiographs based on each view so that any biomedical dysfunction can be more objectively characterized. The films are sequenced with a consistent center of reference. Having a static center of reference allows for the measurement (not just visualization) of the displacement exhibited by occiput, atlas, and axis that result from pure range-of-motion. Using these measurements, restricted motion can be characterized numerically which will increase the objectivity of the assessment.

Further still, an animation sequence can be used to determine which plane of motion (lateral flexion or rotation) as visualized through different radiographic views (e.g. APOM, nasium, base posterior, or vertex) would most clearly demonstrate upper cervical biomechanics when sequenced through computer animation. As an illustrative example, a method of creating a radiographic animation sequence for this purpose is described. In this example, a range-of-motion sequence will comprise five films:

1) one film is of the patient in his or her "neutral" posture (N);
2) one film is of the patient with the head tilt/rotation taken out (i.e. a "forced-0°" film (0));
3) one film is of the patient taken at the right end-range (RE);
4) one film is of the patient taken at the left end-range (LE); and finally,
5) one film is of the patient taken replicating the end-range angle value exhibited by the most restricted direction but on the contralateral side (RR—right restricted or LR—left restricted).

In this example, a lateral cervical film is taken according to the method described above. Next, a lateral flexion range of motion sequence is made based on the APOM view and the nasium view. Then a rotation range of motion sequence is made using the APOM view and the nasium view. The same is made with a base posterior view and a vertex view. The following describes the procedures for taking these radiographic views.

To position the subject patient for a lateral cervical film, the patient faces the Wall Laser Unit 500 with his right shoulder touching the grid cabinet 200. The laser line on the Wall Laser Unit 500 is set to 0° vertical, and the patient is positioned such that the laser line bisects the patient's face. This ensures the absence of head tilt and/or rotation. The two laser lines of the Collimator Laser Unit 400 are set to 0° (vertical) and 90° (horizontal). The patient is translated backwards or forwards using a sliding chair until the laser crosshairs target the C1 transverse process. This ensures that the central ray of the x-ray beam penetrates exactly through C1. The patient's head is flexed or extended until the horizontal aspect of the laser crosshairs intersects the area just beneath the anterior nasal spine (the corner created by the transition between the nose and the infranasal depression or "philtrum"). This ensures that the hard palate is parallel to the bottom edge of the film. This also aids in creating a standard reference for attaining the atlas plane line and a reproducible head position when taking the rest of the films. All angles calculated from this film depend on this sagital plane position.

Next, five films are taken in series to capture lateral flexion as seen through the APOM view.

The first film is taken with the patient's head positioned in its neutral posture (N). The standard APOM view protocols are followed with respect to tube-tilt, grid cabinet tilt, and focal film distance. Laser positioning is as follows: (1) The Wall Laser Unit 500 is set to 90° horizontal and made to intersect the subject at the C1 transverse process (with the subject's head flexed or extended so that this laser line also intersects the anterior nasal spine as in the lateral film); (2) the Overhead Laser Unit 700 is set to 0° coronal and projected onto the subject's head (with the subject being rotated using the movable chair so that the laser line from the overhead unit projects precisely onto the patient's headband); (3) the horizontal laser line on the Collimator Laser Unit 400 is set to 90° horizontal and the tube is positioned so that this line projects just beneath the subject's lower lip (mouth closed) and slightly upwards to intersect the C1 transverse processes; (4) the vertical laser line on the Collimator Laser Unit 400 is made to bisect the subject's face and the value of this angle (neutral head tilt) is recorded. The subject is asked to open his mouth, the exposure is made and the film is labeled "lateral flexion APOM in Neutral" along with the direction and angle of head tilt.

The "forced-0°" (0) film is taken next. The subject remains in the same position as in the previous "neutral" film. The vertical laser line of the Collimator Laser Unit 400 is set to 0° vertical and the subject's head is tilted carefully towards this laser line until the laser line bisects the face precisely ensuring that all other laser lines (from the Overhead Laser Unit 700 and the Wall Laser Unit 500) remain the same. The subject is asked to open his mouth, the exposure is made, and this film is labeled "lateral flexion APOM forced-0°".

Next, the angle and direction of most restricted lateral flexion is determined and at the same time both "End Range" films are taken. The setup remains identical to the previous film. With the subject's third cervical held in place, and the subject's chin held in place, the subject's head is tilted as much as possible to the right and that position is held. The laser lines projected by both the Overhead Laser Unit 700 and the Wall Laser Unit 500 remain in their original positions on the subject to ensure that the subject has not rotated, flexed, or extended the head in the process of lateral tilting. The vertical laser line of the Collimator Laser Unit 400 is then made to bisect the subjects face precisely. The value of this angle is read from the calibrated markings on the device and recorded as "lateral flexion Right End-Range Angle". The subject is asked to open his mouth, the exposure is made, and this film is labeled "lateral flexion APOM Right End-Range". This procedure is repeated with the subject tilting his head to the left. This angle value is recorded as "lateral flexion Left End-Range Angle" and the film is labeled "lateral flexion APOM Left End-Range". The angle values recorded are compared; the lesser angle value is designated as the "Restricted Angle" and used in the next film.

Lastly, the "Restricted" film is taken. The "Restricted Angle" value determined above is used to take this film. The vertical laser line of the Collimator Laser Unit 400 is set to this angle value but opposite the restricted direction. For example, if the lesser angle value and direction are exhibited by right lateral flexion, the restricted film will have the subject in left lateral flexion at the same angle value. The calibrated markings on the Collimator Laser Unit 400 ensure the accuracy of the subject's position at this angle. The subject's head is carefully tilted towards this laser line until it bisects his face precisely. The laser lines projected by both the Overhead Laser Unit 700 and the Wall Laser Unit 500 remain in their original positions on the subject. The subject is asked to open his mouth, the exposure is made, and this film is labeled "lateral flexion APOM (Left or Right) Restricted".

The following describes five films taken in series to capture rotation as seen through the APOM view.

To capture rotation as seen through the APOM view, two coronal reference lines are used in this procedure: one is represented by the thin headband described above; the other is represented by corresponding lines drawn onto the wide shoulder flaps of the lead apron the subject wears throughout the procedure. (When the apron is placed upon the subject, these lines will superimpose across the top of each shoulder in line with the headband). The subject faces the x-ray tube precisely in each film; rotation is induced by rotating the chair upon which the subject sits in the opposite direction of the desired head rotation. The angle of rotation is measured (or positioned) by lining up the laser line projected by the Overhead Laser Unit 700 with the reference lines on the subject's shoulders.

First, the "Neutral" film is taken by repeating the procedure described above with the addition of aligning the Overhead Laser Unit 700 laser line with the subject's shoulders, noting the value and direction of this angle, and labeling the film "rotation APOM Neutral".

Next, the "forced-0°" film is taken. Starting with the subject in the neutral position, all laser components are set to 0°. The subject is carefully positioned such that the Overhead Laser Unit 700 laser line projects across both the headband and the shoulder line. The Collimator Laser Unit's 400 vertical laser bisects the face precisely. The Wall Laser Unit 500 laser connects the C1 transverse process to the anterior nasal spine. The film is taken and labeled "rotation APOM forced-0°".

Next, the angle and direction of most restricted upper cervical rotation are determined and at the same time the "End Range" films are captured. Starting with the subject in the forced-0° position, the subject is instructed to keep facing the x-ray tube 100. The chair is rotated towards the left to the point just before the subject loses his forward-facing orientation (this will induce the end range of right cervical rotation). The Overhead Laser Unit 700 laser is made to coincide with the shoulder lines and this angle is read and recorded as "rotation Right End Range Angle". Ensuring that the subject remains static with respect to the other laser units, he will be asked to open his mouth, and the film is taken and labeled "rotation Right End Range". This procedure is repeated with the contralateral side, recorded and labeled accordingly. The angle values are compared. The lesser value and direction are designated as the "Restricted Angle" used in the next film.

Lastly, the "Restricted" film is taken. The "Restricted Angle" value determined above is used to take this film. The Overhead Laser Unit 700 laser line is set to this angle value but opposite the restricted direction. For example, if the lesser angle value and direction is exhibited by right rotation, the restricted film will have the subject in left rotation at the same angle value. The calibrated markings on the Overhead Laser Unit 700 ensure the accuracy of the subject's position at this angle. The chair is rotated toward this laser line until it lines up with the subject's shoulders. The laser lines projected by both the Collimator Laser Unit 400 and the Wall Laser Unit 500 remain in their original positions on the subject. The subject is asked to open his mouth, the exposure is made, and the film is labeled "rotation APOM (Left or Right) Restricted".

The following describes five films taken in series to capture rotation as seen through the base posterior view.

Again, a neutral film is captured by having the subject face forward. The procedure for setting up this film is as described above. The grid cabinet is angled facing downward at 45° and the subject is positioned so that the center of the grid cabinet 200 coincides with his vertex. The Wall Laser Unit 400 laser line is set to 0° and projected to coincide with the C1 transverse process. The subject's head is flexed or extended until this line also intersects the anterior nasal spine. With the x-ray tube 100 tilted upward, the horizontal laser line component of the Collimator Laser Unit 400 is set to 90° and the x-ray tube 100 is positioned such that this line projects underneath the subject's chin connecting one C1 transverse processes to the other. The vertical component of the Collimator Laser Unit 400 is made to align with the center/tip of the subject's chin. This angle value is recorded as "rotation Neutral Angle". The film is captured and labeled "rotation Base Posterior Neutral".

Next, the "forced-0°" film is captured. With the subject in the neutral position, the vertical laser line of the Collimator Laser Unit 400 is set to 0°. The subject's chin is carefully rotated towards this line until it aligns with it precisely. The film is captured and labeled "rotation Base Posterior forced-0°".

Next, the angle and direction of most restricted upper cervical rotation are determined and at the same time the "End Range" films are captured. While holding the subject's lower cervical spine in place, the subject rotates his head to the right as much as possible and holds this position. The vertical laser line of the Collimator Laser Unit 400 is made to align with the subject's chin and this angle value is recorded as "rotation Right End Range Angle". The film is captured and labeled "rotation Base Posterior Right End Range". This procedure is repeated with left rotation, recorded and labeled accordingly. The angle values are compared and lesser value and direction are designated as the "Restricted Angle".

Finally, the "Restricted" film is captured. The "Restricted Angle" value determined above is used to take this film. The vertical laser line component of the Collimator Laser Unit 400 is set to this angle but opposite the restricted direction. For example, if lesser angle value and direction is exhibited by right rotation, the restricted film will have the subject in left rotation at the same angle value. The calibrated markings on the Collimator Unit 400 ensure the accuracy of the subject's position at this angle. The subject's chin is rotated towards this laser line until it aligns with it precisely. The film will be captured and labeled "rotation Base Posterior (Left or Right) Restricted".

Using appropriate software, the digital films are imported into a computer and converted into the frames of an animation sequence. Once imported, each film is centered or aligned within its frame so that a consistent reference point is created with respect to each film. For example, in the lateral flexion sequence, the base of the odontoid process (or the center of the C2 vertebral body) serves as this consistent reference point by ensuring that it is placed on the exact same spot in each frame. When the animation is played, all other structures will appear to move while the base of the dens stays in place. With this consistent center point of reference, valid measurements of the displacement of other osseous structures observed from one film to the next can be made and compared bilaterally.

In this example, three animation sequences are created. The first sequence consists of all five films, the second consists of the neutral film along with both end-range films, and the third consists of the forced-0° film along with the restricted films (i.e. the end-range film with the least angular displacement value and its contralateral restricted-angle counterpart).

The data is analyzed to discern the ability of each combination of films and of each view to elucidate biomechanical dysfunction. A measuring protocol is used to analyze the relative linear or angular displacement of osseous structures as they transition between the stages of motion exhibited by the film combination. A mathematical algorithm compares the linear/angular displacements to the angular displacements of the ranges of motion measured during the radiographic procedure. Based on this, the extent and directionality of restricted motion exhibited by the anatomical members of the upper cervical spine can be determined for arriving at a chiropractic listing based on biomechanics as opposed to the conventional static misalignment in the neutral position.

I claim:

1. A radiographic apparatus with laser positioning system comprising:
an x-ray generator, said x-ray generator capable of projecting an x-ray beam in a first lateral direction;
a receptor, said receptor positioned in alignment with said generator in said first lateral direction for receiving said x-ray beam;
a first laser unit, said first laser unit mounted on said x-ray generator and capable of projecting a laser beam aligned with said x-ray beam in said first lateral direction;
said first laser unit having two emitters, each of said emitters capable of projecting a laser beam in said first lateral direction;
said two emitters being independently and movably mounted on a curved track; said curved track being affixed to a collimator such that the center of said track coincides with said x-ray beam of said x-ray generator;
a second laser unit, said second laser unit mounted on a side of said receptor such that said second laser unit is capable of projecting a laser beam in a second lateral direction that is orthogonal to said first lateral direction;
a third laser unit, said third laser unit mounted above said receptor such that said third laser unit is capable of projecting a laser beam in a vertical direction that is orthogonal to said first lateral direction and said second lateral direction.

2. A radiographic apparatus with laser positioning system according to claim 1 further comprising a movable platform interposed between said x-ray generator and said receptor for accommodating a subject patient.

3. A radiographic apparatus with laser positioning system according to claim 2 further comprising a frame for mounting said x-ray generator and said receptor.

4. A radiographic apparatus with laser positioning system according to claim 3 wherein said x-ray generator is movably mounted to a first member of said frame.

5. A radiographic apparatus with laser positioning system according to claim 4 wherein said receptor is movably mounted to a second member of said frame.

6. A radiographic apparatus with laser positioning system according to claim 5 wherein said third laser unit is movably mounted to a third member of said frame, said third member being perpendicularly connected to said second member, such that said third laser unit is movable in parallel to said first lateral direction.

7. A radiographic apparatus with laser positioning system according to claim 1 wherein said track has graduated markings along its edge representing angular measurements that allow for the positioning of each emitter at any angle in respect to the center of said track.

8. A radiographic apparatus with laser positioning system according to claim 1 wherein said second laser unit is mounted on a set of tracks that allows said second laser unit to translate vertically and horizontally.

9. A radiographic apparatus with laser positioning system according to claim 8 wherein said second laser unit has a laser emitter mounted on a rotatable circular base plate that allows it to pivot.

10. A radiographic apparatus with laser positioning system according to claim 1 wherein said third laser unit is movably mounted to a track above said x-ray generator and said receptor.

* * * * *